United States Patent
Glaug et al.

(10) Patent No.: US 6,509,513 B2
(45) Date of Patent: *Jan. 21, 2003

(54) ABSORBENT ARTICLE WITH IMPROVED FLUID ACQUISITION SYSTEM

(75) Inventors: Frank S. Glaug, Chester Springs, PA (US); William H. Cook, Cream Ridge, NJ (US); Joan Rodgers, Brookhaven, PA (US); Ruth Levy, Collegeville, PA (US)

(73) Assignee: Tyco Healthcare Retail Services AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/847,911

(22) Filed: May 2, 2001

(65) Prior Publication Data

US 2001/0027302 A1 Oct. 4, 2001

Related U.S. Application Data

(63) Continuation-in-part of application No. 09/439,793, filed on Nov. 12, 1999.

(51) Int. Cl.[7] .................................................. A61F 13/15
(52) U.S. Cl. ........................................ 604/383; 604/378
(58) Field of Search ................................ 604/378, 383

(56) References Cited

U.S. PATENT DOCUMENTS

| | | | |
|---|---|---|---|
| 3,929,135 A | 12/1975 | Thompson | |
| 3,965,906 A | * 6/1976 | Karami | 604/378 |
| 3,994,299 A | * 11/1976 | Karami | 604/378 |
| 4,014,341 A | * 3/1977 | Karami | 604/378 |
| 4,055,180 A | * 10/1977 | Karami | 604/368 |
| 4,184,902 A | * 1/1980 | Karami | 604/378 |
| 4,282,874 A | * 8/1981 | Mesek | 604/365 |
| 4,324,246 A | 4/1982 | Mullane et al. | |
| 4,324,247 A | * 4/1982 | Aziz | 604/371 |
| 4,327,730 A | 5/1982 | Sorensen | |
| 4,463,045 A | 7/1984 | Ahr et al. | |
| 4,552,709 A | 11/1985 | Koger, II et al. | |
| 4,601,868 A | 7/1986 | Radel et al. | |
| 4,609,518 A | 9/1986 | Curro et al. | |
| 4,629,643 A | 12/1986 | Curro et al. | |
| 4,690,679 A | 9/1987 | Mattingly, II et al. | |

(List continued on next page.)

FOREIGN PATENT DOCUMENTS

| | | | | |
|---|---|---|---|---|
| EP | 0207904 | 1/1987 | | |
| EP | 0596532 | 5/1994 | | |
| GB | 2294901 | 5/1996 | | |
| WO | WO 9218078 | 10/1992 | | |
| WO | WO-93/09741 | * 5/1993 | | 604/378 |
| WO | WO9309744 | 5/1993 | | |

Primary Examiner—Aaron J. Lewis
Assistant Examiner—C Lynne Anderson
(74) Attorney, Agent, or Firm—Caesar, Rivise, Bernstein, Cohen & Pokotilow, Ltd.

(57) ABSTRACT

A disposable absorbent article, e.g., a diaper, arranged to be worn by a wearer to trap and collect fluid waste products. The article has a flexible chassis made up of a top-sheet, a two layer fluid acquisition system, and a fluid absorbent core.

19 Claims, 7 Drawing Sheets

U.S. PATENT DOCUMENTS

| | | | |
|---|---|---|---|
| 4,695,278 A | 9/1987 | Lawson | |
| 4,726,976 A | 2/1988 | Karami et al. | |
| 4,738,675 A | 4/1988 | Buckley et al. | |
| 4,764,234 A | 8/1988 | Smits et al. | |
| 4,764,242 A | 8/1988 | Gressick et al. | |
| 4,780,352 A | 10/1988 | Palumbo | |
| 4,795,451 A | 1/1989 | Buckley | |
| 4,795,454 A | 1/1989 | Dragoo | |
| 4,804,379 A | 2/1989 | Toth et al. | |
| 4,806,411 A | 2/1989 | Mattingly, II et al. | |
| 4,900,318 A | 2/1990 | Toth | |
| 4,988,344 A | 1/1991 | Reising et al. | |
| 4,994,037 A | 2/1991 | Bernardin | |
| 5,231,122 A | 7/1993 | Palumbo et al. | |
| 5,261,899 A * | 11/1993 | Visscher et al. | 604/358 |
| 5,263,948 A | 11/1993 | Karami et al. | |
| 5,263,949 A | 11/1993 | Karami et al. | |
| 5,294,478 A | 3/1994 | Wanek et al. | |
| 5,300,054 A | 4/1994 | Feist et al. | |
| 5,304,161 A | 4/1994 | Noel et al. | |
| 5,308,344 A | 5/1994 | Toth | |
| 5,387,208 A | 2/1995 | Ashton et al. | |
| D363,120 S | 10/1995 | Suskind et al. | |
| 5,460,622 A | 10/1995 | Dragoo et al. | |
| D364,040 S | 11/1995 | Suskind | |
| 5,486,167 A | 1/1996 | Dragoo et al. | |
| 5,514,105 A | 5/1996 | Goodman, Jr. et al. | |
| 5,520,673 A | 5/1996 | Yarbrough et al. | |
| 5,522,809 A | 6/1996 | Larsonneur | |
| H1575 H | 8/1996 | Daugherty et al. | |
| 5,558,655 A | 9/1996 | Jezzi et al. | |
| 5,591,149 A | 1/1997 | Cree et al. | |
| 5,599,344 A | 2/1997 | Johnston et al. | |
| 5,603,707 A | 2/1997 | Trombetta et al. | |
| 5,607,414 A | 3/1997 | Richards et al. | |
| 5,609,588 A | 3/1997 | DePalma et al. | |
| 5,648,142 A * | 7/1997 | Phillips | 428/132 |
| 5,667,864 A * | 9/1997 | Landoll | 604/383 |
| 5,674,211 A * | 10/1997 | Ekdahl | 264/504 |
| 5,681,300 A | 10/1997 | Ahr et al. | |
| 5,693,037 A * | 12/1997 | Lee et al. | 604/378 |
| 5,730,737 A | 3/1998 | Widlund et al. | |
| 5,752,945 A | 5/1998 | Mosley et al. | |
| 5,817,081 A | 10/1998 | LaVon et al. | |
| 5,820,615 A | 10/1998 | Koczab | |
| 5,827,254 A | 10/1998 | Trombetta et al. | |
| 5,830,555 A * | 11/1998 | Srinivasan et al. | 428/131 |
| 5,833,678 A | 11/1998 | Ashton et al. | |
| 5,843,055 A | 12/1998 | Seger | |
| 5,855,572 A | 1/1999 | Schmidt | |
| 5,891,120 A | 4/1999 | Chmielewski | |
| 5,895,379 A | 4/1999 | Litchholt et al. | |
| 5,906,602 A | 5/1999 | Weber et al. | |
| 5,935,682 A * | 8/1999 | Wallstrom | 428/137 |
| 5,998,696 A | 12/1999 | Schone | |

\* cited by examiner

ABSORBENT ARTICLE WITH IMPROVED FLUID ACQUISITION SYSTEM

RELATED APPLICATION

This application is a Continuation-In-Part of U.S. patent application Ser. No. 09/439,793, filed on Nov. 12, 1999, entitled Absorbent Article with Improved Fluid Acquisition System which is assigned to the same assignee as this invention, and whose disclosure is incorporated by reference herein.

FIELD OF THE INVENTION

This invention relates generally to disposable absorbent articles and more specifically to disposable absorbent articles, e.g., diapers, which exhibit enhanced liquid absorption and trapping characteristics.

BACKGROUND OF THE INVENTION

Disposable absorbent articles, e.g., diapers, catamenial pads, panty liners, shields, etc., frequently make use of a liquid absorbent core located between a top-sheet and a back sheet. The top-sheet is commonly formed of a material which is pervious to body fluids, e.g., urine, to promote the transfer of such fluids into the core with minimal fluid retention by the top-sheet. The back-sheet is commonly formed of a liquid impervious or hydrophobic material to form a barrier wall so that any fluid absorbed by the article cannot escape out the back-sheet. In many cases, a fluid "acquisition," "surge" or "transfer" layer is located between the top-sheet and the core to facilitate the transference of body fluid(s) into the core.

In some applications the top-sheet of the disposable absorbent article is formed a woven, non-woven or carded fibrous web. In other cases a perforated or apertured polymeric film is used in place of the fibrous web top-sheet. Typically most of such apertured films are of a three dimensional nature, e.g., they are embossed and/or debossed to include numerous protuberances, channels, capillaries, hills and valleys, etc. Such three dimensional apertured film top-sheets exhibit a pleasing soft, cloth-like appearance similar to that of the prior art woven, non-woven or carded fibrous webs, while providing for a quick and efficient transfer of liquid therethrough to the underlying absorbent layer(s).

Examples of perforated three dimensional film top-sheets are found in U.S. Pat. No. 3,929,135 (Thompson), U.S. Pat. No. 4,324,246 (Mullane et al.), U.S. Pat. No. 4,327,730 (Sorensen), U.S. Pat. No. 4,463,045 (Ahr et al), U.S. Pat. No. 4,552,709 (Koger et al.), U.S. Pat. No. 4,601,868 (Radel), U.S. Pat. No. 4,609,518 (Curro et al.), U.S. Pat. No. 4,629,643 (Curro et al.), U.S. Pat. No. 4,690,679 (Mattingly, III et al.), U.S. Pat. No. 4,806,411 (Mattingly, III et al.), U.S. Pat. No. 5,514,105 (Goodman et al.), D362,120 (Suskind et al), and D364,040 (Suskind), and in United States Statutory Invention Registration H1575 (Daugherty et al.).

The absorbent core of many disposable diapers and other higher performance incontinence products, e.g., adult briefs, typically have cores with enhanced absorbency capability. This enhanced absorbency can be accomplished by use of an air-laid super absorbent material, or by the inclusion of absorbency enhancers, e.g., materials sometimes referred to as "super-absorbent-polymers" (which may be in the form of particles or fibers) with other absorbent materials, such as a fluff, e.g., comminuted wood pulp or other cellulosic fibers. Examples of super absorbent materials are hydrogel polymer particulates, sometimes referred to as "SAP," and hydrogel polymer fibers, sometimes referred to as "SAF." The fluff for the core serves as a means for quickly absorbing the liquid transferred to it. Unfortunately, while fluff is suitable for the task of quick absorption it is somewhat deficient from the standpoint of liquid retention and ability to accommodate repeated insults. SAP on the other hand, has the ability to retain absorbed liquid and to handle repeated insults. The drawback with SAP and SAF are their slowness in absorbing liquid. Accordingly, heretofore disposable absorbent articles have typically taken two approaches to ensure efficient action. In particular, they have included a higher ratio of SAP to fluff to facilitate the rapid absorption of the liquid by the fluff of the core until to SAP can absorb and trap it, and have also included an the heretofore mentioned acquisition or surge layer (also sometimes called a "transfer" layer) disposed over the core. Acquisition layers have typically been constructed of a woven, non-woven or carded fibrous material. They are arranged to quickly absorb the liquid through the absorbent article's cover stock, liner, or top-sheet for temporary retention (e.g., to act as a temporary reservoir), and to transfer that liquid into the underlying core at a rate at which the core can absorb for final or permanent retention. In particular, an acquisition layer improves "wicking" of the absorbent article by spreading the body fluid in the "x" and "y" plane over the area of the core encompassed by the acquisition layer while also carrying the fluid in the "z" direction to the core.

Examples of prior art acquisition layers are disclosed in U.S. Pat. No. 4,988,344 (Reising et al.), U.S. Pat. No. 4,994,037 (Bernardin), U.S. Pat. No. 5,294,478 (Wanek et al.), U.S. Pat. No. 5,300,054 (Feist et al.), U.S. Pat. No. 5,304,161 (Noel et al.), U.S. Pat. No. 5,387,208 (Ashton et al.), U.S. Pat. No. 5,460,622 (Dragoo et al.), U.S. Pat. No. 5,486,167 (Dragoo et al.), U.S. Pat. No. 5,520,673 (Yarbrough et al.), U.S. Pat. No. 5,522,809 (Larsonneur), U.S. Pat. No. 5,558,655 (Jezzi et al.), U.S. Pat. No. 5,591,149 (Cree et al.), U.S. Pat. No. 5,607,414 (Richards et al.), U.S. Pat. No. 5,609,588 (DiPalma et al.), U.S. Pat. No. 5,730,737 (Widlund et al.), U.S. Pat. No. 5,752,945 (Mosley et al.), U.S. Pat. No. 5,833,678 (Ashton et al.), U.S. Pat. No. 5,843,055 (Seger), U.S. Pat. No. 5,855,572 (Schmidt), U.S. Pat. No. 5,895,379 (Litchholt et al.), and U.S. Pat. No. 5,906,602 (Weber et al.). Examples of commercially available materials used for acquisition layers in disposable absorbent articles are through-air bond staple fibers, adhesively bonded staple fibers, and thermally point bonded staple fibers.

As will be appreciated by those skilled in the art increasing the SAP (or other absorption enhancing material) to fluff ratio to provide an absorbent product, e.g., diaper, suitable for accommodating multiple insults of body fluids would concomitantly place an additional burden on the liquid acquisition layer to facilitate transfer of the liquid at a rate that the SAP/other absorption enhancing material could accommodate. Heretofore the materials making up the prior art liquid acquisition layers have provided less than desired results.

Accordingly a need exists for a diaper or other high capacity absorbent article making use of a relatively high SAP/other absorption enhancing material content core and an effective liquid acquisition system to transfer the liquid into the core.

Various absorbent articles which are commercially available have made use of various layers of materials. For example, sanitary pads made by The Kendall Confab Retail Group and sold under the trademark EVERYDAY PANT- ILINER have included a top sheet formed of a fibrous material over the marginal edges of the pad, but not over the intake or "target" zone (i.e., the area at which the body fluid(s) gain(s) ingress into the absorbent article), a three dimensional apertured film forming the top layer of the intake/target zone, a fluid acquisition layer formed of a fibrous material (non-woven) web, and a core formed of an air laid web containing super absorbent material. Other pads in the form of Ultra Thins are also made by The Kendall Confab Retail Group and sold under trademark FRESH TIMES have included a top sheet formed of an apertured film, an air-laid acquisition layer and a core formed of a combination of air-laid and SAP or an air laid super absorbent material. Still other pads in the form of Contour Maxi pads are made by The Kendall Confab Retail Group and sold under the trademark FRESH TIMES have included a top sheet formed of an apertured film and a core formed fluff. Still other pads in the form of Maxi pads are made by The Kendall Confab Retail Group and sold under the trademark FRESH TIMES have included a top sheet formed of a fibrous material, a tissue fluid acquisition layer and a core formed of fluff. Diapers made by The Kendall Confab Retail Group and sold under the trademark HAPPIES have included a non-woven top sheet, a through-air-bonded (or non-woven) acquisition layer, a tissue layer, and an absorbent core made of fluff and SAP.

While all of the foregoing articles are suitable for their intended purposes, they never the less leave something to be desired from the standpoint of fluid retention capacity and fluid transfer into a high capacity core.

SUMMARY OF THE INVENTION

A disposable absorbent article, e.g., a diaper, which is arranged to be worn by a person to trap and collect fluid waste products, e.g., urine. The absorbent article is suitable for accommodating multiple insults of such fluid(s) without leakage, while also exhibiting good strike-through and re-wet properties.

The absorbent article basically comprises a top-sheet, a fluid acquisition system, and an absorbent core. The top-sheet includes a portion which forms the fluid intake or target zone of the absorbent article, with that portion of the top sheet being formed of a liquid pervious, e.g., hydrophilic, material. The fluid intake or target zone makes up a portion of the area of the absorbent core. The absorbent core is formed of a material suitable for accommodating multiple insults of the fluid waste products, e.g., comprises fluff and super absorbent materials for good fluid retention.

The fluid system comprises a first fluid acquisition layer and a second fluid acquisition layer. The first fluid acquisition layer is located below the fluid intake zone portion of the top-sheet and over the second liquid acquisition layer. The first liquid acquisition layer is formed of an apertured film, e.g., a three dimensional apertured film. The second fluid acquisition layer is formed of a fibrous, fluid pervious material, e.g., a non-woven. The second fluid acquisition layer is located over the absorbent core. At least one of the first and second acquisition layers is at least coextensive in size with the fluid intake zone.

The fluid acquisition system cooperates with the core to facilitate the transference of fluid, e.g., urine, into the core for absorption and retention in the core even under repeated insults.

When the absorbent article is in the form of a diaper it also preferably includes a back-sheet formed of a fluid impervious material.

DETAILED DESCRIPTION OF THE PREFERRED EMBODIMENT

Figure 1:
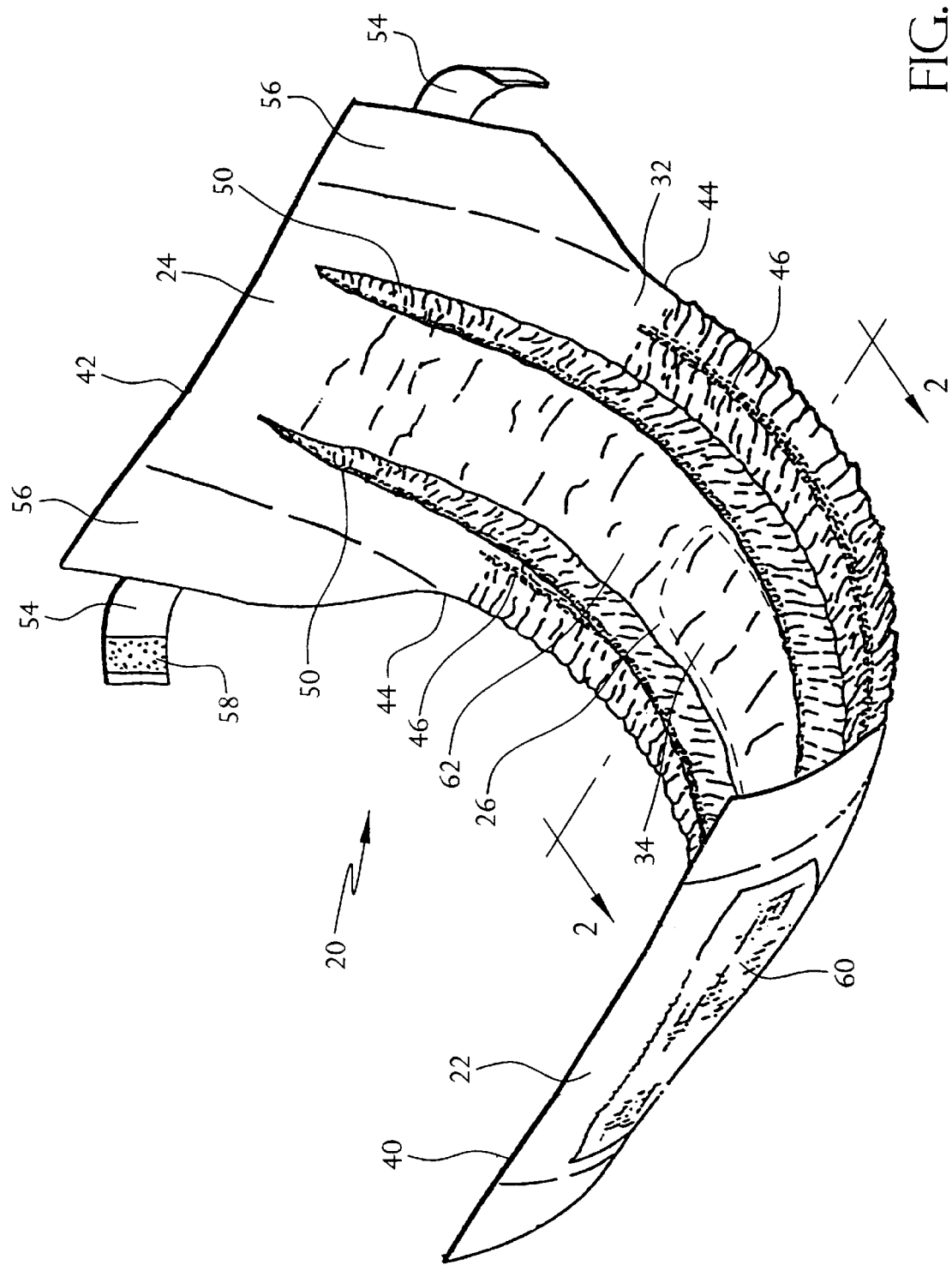
FIG. 1 is an isometric view of one preferred embodiment of an absorbent article, e.g., a diaper, constructed in accordance with the subject invention.

Referring now to the various figures of the drawing wherein like reference characters refer to like parts, there is shown in FIG. 1 a disposable absorbent article 20 constructed in accordance with one embodiment of this invention. It should be pointed out that as used herein the term "disposable" means that article is designed to be used until soiled, either by urination or otherwise, and then discarded, rather than being washed and used again.

In the embodiment of FIG. 1 the article 20 is in the form of a diaper. While the following description will focus on diapers, it should be clear that the subject invention can be used for any type of absorbent article or garment to be worn by a person for trapping urine or menses.

Figure 2:
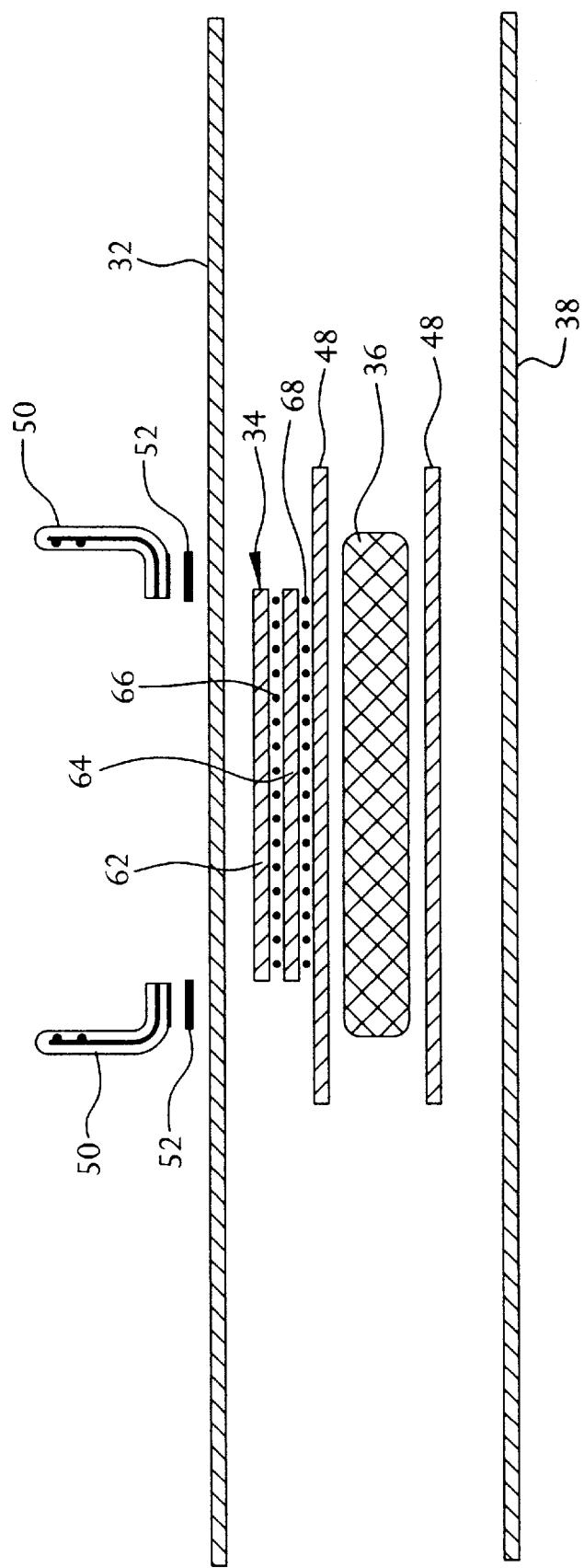
FIG. 2 is an enlarged, exploded sectional view taken along line 2—2 of FIG. 1.

The diaper 20 basically comprises a chassis including a front waist portion 22, a back waist portion 24, and a crotch portion 26 and is of generally conventional construction, except for the inclusion of fluid acquisition system for effectively transferring received body fluid(s) to an absorbent core capable of handling repeated insults of the fluid(s). In the exemplary embodiment to be described hereinafter the core includes a higher proportion of liquid-absorption-enhancing materials, e.g., SAP, in its absorbent core than commonly used in the prior art. Those components of the diaper 20 will be described in detail later. Prior to describing those components a brief description of the other portions of the diaper will now be discussed. To that end and as best seen in FIG. 2, the diaper 20 basically comprises a body-side liner or top-sheet 32, the heretofore mentioned fluid acquisition system 34 (to be described later), a liquid absorbent structure or core 36 including liquid-absorption-enhancing materials (to be described later), and an outer cover or back-sheet 38.

The top-sheet 32 is arranged to face toward the body of the user, when the diaper is in place, with the back-sheet facing away from the wearer. The top-sheet is superimposed over the back-sheet, with the absorbent core 36 interposed therebetween. The fluid-acquisition system 34 is located on top of the core and under the top-sheet to facilitate the passage of liquid waste into the core for absorption thereby. The top-sheet 32 and/or back-sheet 38 can be any suitable shape and dimensions for other designs or constructions, as will be clear from the other embodiments disclosed herein.

The back-sheet 38 comprises front edge 40, a back edge 42, and a pair of side edges 44. Each side edge includes a central, cut-out to define a respective leg cut out. The crotch portion 26 of the diaper is located between the leg cut-outs.

The top-sheet 32 may be of the same shape as the back-sheet 38 or of a different shape and is bonded to the back-sheet 36 around its entire periphery, with the absorbent material core 36 and the fluid acquisition system 34 interposed therebetween. The back-sheet and top-sheet can be joined together in any suitable manner, e.g, by adhesive bonding. The adhesives can be applied in any manner such as by spraying, slot-coat extrusion, printing, or the like. The applied adhesive can be in any desired configuration or design, such as continuous or discontinuous beads, continuous or discontinuous swirls, meltblown patterns, spray patterns, or the like. Alternatively, the joining of layers and structures can be accomplished by heat sealing, ultrasonic bonding, or the like.

Each lateral side edge 44 of the diaper 20 is elasticized by means of plural, e.g., three, longitudinally extending elastic, e.g., LYCRA 940 decitex, threads or strands 46 disposed along the length of the cut away portion of that side edge. The strands may be attained from E.I. DuPont de Nemours and Company, Wilmington, Del., and are held in place by a suitable elastic adhesive, such as that used to hold the elastic foam of the waist portion in place. The elastic adhesive is intermittently applied along the top sheet to allow the diaper to be actively stretchable along the leg cut outs and not all the way to the edges of the respective waist portions, thereby enable the diaper to closely conform about the legs of the wearer for impeding the egress of waste material from the crotch region, as is conventional. Other arrangements can be used to elasticize the sides of the crotch portion of the diaper. For example, in lieu of plural longitudinally extending elastic threads 46, multiple strands of elastic material can be arranged in other orientations, intersecting, diagonal, or any combination thereof, or can be a film or laminate of various types of elastomeric material.

The back-sheet 38 or cover is preferably formed of a laminated sheet of a nonwoven material and film (with the non-woven side positioned as the outermost layer). Such material should be hydrophobic, soft in texture, and strong in tensile strength. One particularly suitable material is a spunbond-meltblow-spunbond (SMS) web having a basis weight of about 15 gms per square meter (gsm), available from AVGOL Nonwoven Industries LTD., Holon, Israel.

The spunbond layer is made of polypropylene fibers. Such composites provide the dual advantages of liquid barrier properties of film along with a soft, warm outer fabric texture. The non-woven outer cover can also be made of other suitable cloth-like materials, e.g., spun-bond or thermal-bond non-woven web made of either polypropylene, polyethylene, polyester, bi-component fibers (polyethylene/polypropylene or polyethylene/polyester), or any combinations of these fibers. Various multiple layer configurations or fiber denier variations may be used. Another example includes hydro-entangled non-woven webs, which may contain some cotton and/or rayon fibers blending in with thermal-plastic fibers. Cellulose fibers can also be blended in at small percentages to reduce cost. Still another example is a non-woven outer-cover made of stretchable or elastic materials, such as elastomeric composites of non-woven(s) and elastic membranes or a single layer of elastic material. The elastomeric composite can comprise of an inner layer of pre-stretched extruded elastic film sandwiched between and attached to a pair of non-woven webs. The non-woven webs may consist of spun-bond web, thermal-bond web, or a combination of the two. Preferably, the elastic film is made of synthetic rubber and the non-woven made of spun-bond polypropylene.

Other materials for forming the back-sheet 38 may include polypropylene films, co-extruded films (polyethylene and ethylene vinyl acetate), co-polymer films (polyethylene/polypropylene), and polylaminates (polypropylene nonwoven and polyethylene film). Still another example is a film made of a "breathable" microporous polyethylene. Suitable breathable films are available from Exxon Chemical Company, Buffalo Grove, Ill. This material allows water vapor to pass through it over time, while being impervious to liquid water. The water vapor transmission rate may range from 200–2000 grams per square meter per 24-hour period.

The fluid-acquisition system 34 will be described in considerable detail later. Suffice it for now to state that it includes at least two layers of materials which are constructed such that they cooperate to manage, transport, accommodate and/or direct high volumes and high flow rates of urine or other body fluid received from the top sheet target zone into the absorbent core 36 at a rate that the core can handle, despite multiple insults of such fluid.

In order to enable urine to quickly and efficiently pass through the top-sheet and into the underlying acquisition system 34 for subsequent transference to the absorbent core 36 for trapping therein, the top-sheet 32 is preferably liquid permeable. In particular, the top sheet may be selected from a variety of textile-like films and fabrics. Suitable fabrics include non-woven materials that are pervious to liquid, soft and pliable. Preferred non-woven materials include spun-bonded polypropylene; spunbonded polyethylene; thermally bonded webs of staple fibers preferably polypropylene shape or sheath/core bi-component fibers having a core of polyester or polypropylene and a sheath of polyethylene. To enhance the fluid control properties of the aforementioned liners, surfactants or wetting agents typified by X-100 and Triton X-102 available from Rohm & Haas Company of Philadelphia, Pa. may be applied to the fluid receiving zones of the liner selectively having the outer zones untreated to reduce migration excreted fluid such as urine into the outer diaper regions leading to diaper leakage.

If desired, the top sheet 32 may be formed of a liquid impermeable material having plural apertures or pores extending therethrough so as to make the material liquid permeable.

The absorbent core 36 is a rectangular member which is centered in the diaper and extends from close to the front waist edge to close to the back waist edge. The core can be made up of any suitable absorbent material, as well as combinations of different types of absorbent material(s). For example, in the preferred embodiment of FIG. 1 the absorbent core 36 is formed of a mixture of pulp fluff and SAP wrapped in a liquid permeable tissue wrap 48 (only two sheets of which are shown in FIG. 2). Examples of SAP include polyacrylamides, polyvinyl alcohol, polyacrylates, various grafted starches, and the like. A desired super absorbent material is a cross-linked polysodium acrylate, which can be purchased from Chemdal Corporation, Palatine, Ill., under the trademark ASAP 2260. The super absorbent materials can be in various geometric forms, such as various shaped particles, fibers, foams, and layers. The fluff and SAP are present in a ratio of about 11.5 grams of SAP to 16.5 gms of fluff for a size 4 diaper, and have a core density range of about 0.16 to 0.18 grams per cubic centimeter.

Moreover, the core 36 can be of any shape and can be a single, integral absorbent structure, or can comprise a plurality of individual separate absorbent structures and/or absorbent materials that are operably assembled together. It can also consist of air-laid non-woven web that contains super-absorbent particles and/or super-absorbent fibers, polymeric binder and cellulose pulp fibers. In one exemplary embodiment the absorbent core is sandwiched between two plies of tissue, is aligned on top of the back-sheet and adhered down with construction adhesive. The tissue has a basis weight of 17.1 gsm. Suitable tissues are available from Cellu Tissue Corporation, East Hartford, Conn. The absorbent core is centered along the transverse direction and registered in the machine (longitudinal) direction within the diaper's chassis.

The amount of each absorbent material and SAP/fluff ratio depends on the size of the brief, e.g., "Small", "Medium", "Large" or "Extra Large" and the construction of the liquid acquisition or transfer system 34.

The diaper 20 also includes a pair of conventional "standing leg gathers" or cuffs 50 or liquid-impervious gaskets to provide leakage control in the crotch region. The standing leg gathers are located so that they extend along the leg opening region of the diaper as disclosed in U.S. Pat. No. 4,695,278 (Lawson) and U.S. Pat. No. 4,795,454 (Dragoo), both of which are incorporated by reference herein. Each standing leg gather is elasticized and extends from the edge of the front waist portion to the edge of the rear waist portion and along a respective side marginal edges of the core 36 and upstanding from the top-sheet 32. The standing leg gathers are secured in place by a suitable adhesive, e.g., construction adhesive 52.

The diaper 20 is arranged to be held in place on the body of the wearer in a conventional manner, e.g., by means of a pair of fastening tabs or tapes 54 projecting outward from a pair of respective ear portions 56 forming the side edges of top sheet 32 of the diaper contiguous with its back waist portion 42. In particular, each tab 54 includes a patch 58 of a myriad of small hooks on its underside surface. Each patch is arranged to be releasably secured to a "landing zone" portion 60 on the outer cover in the front waist region of the diaper. The landing zone is located at a position so that when the diaper is folded in half with the front waist portion disposed opposite the back waist portion, the landing zone 60 will be aligned with the tabs 54.

The landing zone 60 basically comprises a rectangular panel of whose outer surface comprises a myriad of small loops arranged to be engaged by the small hooks of the patch 58 of each fastening tab.

When the diaper is in place on the person with the front waist portion disposed over the lower abdomen, the back waist portion disposed over the lower back and buttocks region, and the crotch portion between the legs, each tab 54 may be brought into engagement with the a portion of the landing zone 60 closest to that tab on the front portion of the diaper so that the myriad of hooks on the patch engage the myriad of loops of the landing zone 60 to releasably secure the tab thereto. Any suitable multi-hook and multi-loop materials may be used. Particularly suitable multi-hook patches 54 are available from YKK (U.S.A.), Inc., Marietta, Ga., under the model designation Microhook (D-7) or Macrohook (EL "B"), while particularly a suitable multiloop material is a polyester fiber material having a basis weight of 1.55 ounce per square yard with a laminated polypropylene film (8 mil.) backing is available from FAB Industries, Inc, New York, N.Y.

Alternatively the tabs 54 may be in the form of adhesive tapes, such as those available from 3M Corporation, St. Paul, Minn., and the landing zone may be formed of a polyester film with a pre-applied adhesive in a selected print pattern, such as also available from 3M Corporation, St. Paul, Minn.

As mentioned earlier, the fluid-acquisition system basically comprises at least two layers disposed over each other. In particular, the uppermost of the layers making up the fluid acquisition system 34 comprises an apertured polymeric film 62, which is preferably three dimensional in nature, e.g., is embossed and/or debossed, like that used heretofore and described above for cover sheets of diapers. One particularly suitable material is available from Tredegar Film Products of Terra Haute, Ind. under the trade designation C120 and basically comprises a polyethylene film apertured like that shown in U.S. Pat. No. D362,120 (Suskind et al.), whose disclosure is incorporated by reference herein. Other three dimensional polymeric apertured films, such as those in the patents discussed above, can be utilized to form the first fluid acquisition layer 62. In fact, for some applications two dimensional apertured films, like those of the prior art, may be used for the layer 62.

The lowermost layer making up the fluid acquisition system 34 is designated by the reference number 64 and can be any type of fibrous material, e.g., a through-air bonded/carded web, a spun-bond bi-component non-woven web, a web of cross-linked cellulosic fibers. One particular suitable material is available from PGI Non-wovens, Landisville, N.J., and has an overall basis weight of 40 gsm, with high denier (10 denier) bi-component fibers situated on the top (facing the top-sheet) and low denier (6 denier) bi-component fibers situated on the bottom (facing the core 36). The bi-component fibers are made of a polypropylene inner core and polyethylene outer sheath.

The uppermost and lowermost layers are preferably, but not mandatorily, adhered or secured together by any suitable adhesive 60 (e.g., a construction adhesive or hydrophillic adhesive, such as Cycloflex adhesive available from National Starch and Chemical, Bridgewater, N.J.

In the embodiment of the fluid acquisition system of FIG. 1 the upper layer 62 is coextensive in size with the lower layer 64, as shown clearly in the reduced size plan view of FIG. 3. The width of the upper and lower layers 62 and 64, respectively, is approximately equal to the width of the core 36 (See FIG. 2). If desired, they can be smaller in width provided that they extend for the width of the target zone (the area that will receive the fluid, e.g., urine, insult when the wearer of the article voids). As will be appreciated by those skilled in the art the target zone of an absorbent article, such as a diaper, a pantiliner, etc., is typically of a smaller area than the absorbent core 36 of that article and is located in a generally centered position with respect to the sides of the core and may be centered or off-centered with respect to the ends of the core. The length of the upper and lower layers 62 and 64 of the acquisition system 34 of the embodiment of FIG. 1 is at least as long as the length of the target zone, and preferably the length of the core 36. In fact, if desired, the two layers can be longer in length to provide an additional measure of protection from leakage along the front or back of the article, particularly when the wearer is laying down and applying pressure to the article.

The fluid-acquisition system 34 is also preferably adhesively secured in place by any suitable adhesive 60 (e.g., a construction adhesive or hydrophillic adhesive, such as Cycloflex adhesive available from National Starch and Chemical, Bridgewater, N.J.). In the exemplary embodiment described above, 16.5 grams of fluff and 11.5 grams of SAP is used for the absorbent core for both the "Medium" and "Large" sizes of diapers, with a transfer or acquisition system including an upper layer 62 of 26.3 gsm, and a lower layer 64, of 20 gsm/70 mm through air bonded bicomponent fibers adhered on top of the absorbent core in a "continuous" configuration. A higher basis weight acquisition layer 64, e.g., 50 gsm/70 mm thermal bonded polypropylene fibers, with a variety of fiber material combinations and deniers, can be also used. The lower layer 64 may be in the range of 10–50 gsm/20–230 mm through air bonded bicomponent fibers. Other high-absorbency materials can also be used for the core, such as super absorbent fibers or peat moss.

The acquisition system 34 can be secured in place by either adhesively securing its upper layer 62 to the top sheet 32 and/or by adhesively securing it lower layer 64 to the core 36. In the exemplary embodiment shown herein the lower layer 64 is secured to the tissue covering 48 of the core.

If desired the core 36 may be held in place by a hydrophillic construction adhesive, such as Cycloflex from National Starch and Chemical Corporation, Bridgewater, N.J. In such an arrangement the adhesive may be applied on undersurface of the lower layer 64 of the acquisition system as well as the inner surface of the back sheet 36.

In order to facilitate the transference of the body fluid(s) through the absorbent article into the core 36, one or more of the various layers may be treated with any suitable surfactant(s), such as a "fast finish" surfactant for the layer 64 and monoglyceride and diglyceride for the layer 62. In the exemplary embodiment the layer 62 treated with a suitable surfactant is available from Tredegar Film Products of Terra Haute, Ind. as X-6958 white C120 apertured film. It should be pointed out at this juncture that in the exemplary embodiment of the diaper shown and described herein both the layers 62 and 64 are treated with surfactants, but either or neither layer may be so treated.

As best seen in FIG. 1 the acquisition system 34 is located in the diaper over the core in the front portion of the diaper making up the fluid intake or target zone of the diaper, i.e., the portion of the diaper to directly receive the liquid body waste(s) from the wearer. If desired the acquisition system 34 can be extended into the rear portion of the diaper, as well.

The absorbent article 20 operates as follows upon the receipt of a fluid (e.g., urine) insult to its top sheet 32 intake zone. The fluid penetrates the top sheet 32 and passes through the apertured polymeric layer (film) 62 of the fluid acquisition sytsem generally perpendicularly to the layer 62. Fluid flow is faster into the diaper 20, i.e., through the top sheet into the diaper, than coming out of the diaper through the top sheet. This is due to the fact that the apertured polymeric film 62 of the exemplary preferred embodiment has three dimensionally shaped apertures directed inwardly towards the core 36. In particular, with the preferred exemplary embodiment the apertured film 62 includes a myriad of very tiny conically shaped apertures, which taper in the direction from the top sheet 32 towards the core 36. This arrangement results in a faster and higher fluid volume intake into the diaper and a slower and lower fluid volume output after the diaper has been saturated with fluid and exposed to compressive forces. The fluid then contacts the lowermost layer 64 of the fluid acquisition system 34, where the fluid experiences some lateral distribution both transversely and longitudinally in the plane making up the layer 64 due to the fiber orientation of that layer in the machine direction. From there the fluid enters into the core for ultimate absorption and retention.

For some applications, where maximum fluid transference is desired the fluid acquisition system 34 may be constructed so that the two layers 62 and 62 are coextensive in size with the core 36. In fact, the two layers may extend for greater than the length of the core, e.g., up to the front and back top edges of the diaper so that they can be cut to length with the cutting of the diaper during the diaper's manufacture. The width of the acquisition system or either or both layers can, if desired, be wider than that of the core. Needless to say a diaper or other absorbent article with a fluid acquisition system encompassing the area of the core or greater, may be somewhat expensive to fabricate. Where cost is an overriding concern the absorbent article of this invention may make use of a lower cost fluid acquisition system 34 than those described above. In particular, as will be appreciated by those skilled in the art, the apertured film forming the upper layer 62 is a somewhat expensive component. Hence, for some applications its size may be smaller than the size of the core 36 or the size of the lower layer 64, so that less of it is required, thereby lowering the cost of the absorbent article. Moreover, for some applications the size of the lower layer of the fluid acquisition system may be smaller than the core or the upper layer, so that less of the non-woven material is necessary, thereby resulting in a lower cost product. Moreover, the non-woven material making up the lower layer 64 may have a lower basis weight in the interest of reducing costs.

Figure 3A:
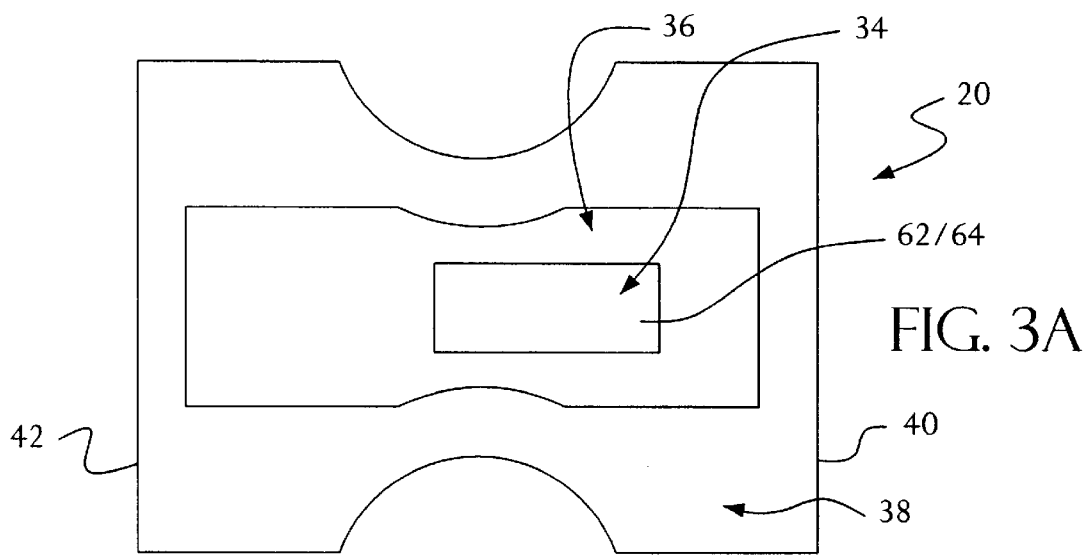
FIG. 3A is a reduced plan view of a diaper, like that of FIG. 1, but utilizing an alternative fluid acquisition system constructed in accordance with this invention.

Thus, in FIGS. 3A et seq. there are shown additional exemplary embodiments of the two layer fluid acquisition system of this invention that are somewhat less expensive than an embodiment whose fluid acquisition system 34 is at least coextensive in size to the core 36. It should be noted that in FIGS. 3A et seq. the top sheet 32 is not shown, it being understood that such a sheet is, however, utilized in place over the top layer of acquisition system 34 in the diaper 20 as described above with reference to the embodiment of FIG. 1.

In FIG. 3A there is shown one of the above mentioned alternative exemplary embodiments of a two layer fluid acquisition system for a diaper 20. In the case of FIG. 3A the diaper 20 is constructed in accordance with this invention and making use of a less expensive fluid acquisition system 34. To that end, both the upper layer 62 and lower layer 64 of the fluid acquisition system 34 are coextensive in size, and of a lesser width and length than the core 36. In particular, the acquisition system 34 is of a size which is coextensive with the target zone (i.e., the area of the diaper that initially receives the fluid insult). As can be seen clearly this zone is somewhat off-center front-to-back with respect to the diaper 20 (i.e., the target zone being located closer to the front edge 40 of the diaper than the back edge 42). The diaper making use of this type of acquisition system can be readily fabricated by cutting the two layers 62 and 64 of the acquisition system 34 to the desired size and then placing them on top of the core 36 at the target zone. As will be appreciated by those skilled in the art, with the acquisition system 34 centered at the target zone, any fluid insult received by the diaper will be immediately directed into the core at the center of the core (the area making up the target zone) and from there spread throughout the core.

Figure 3B:
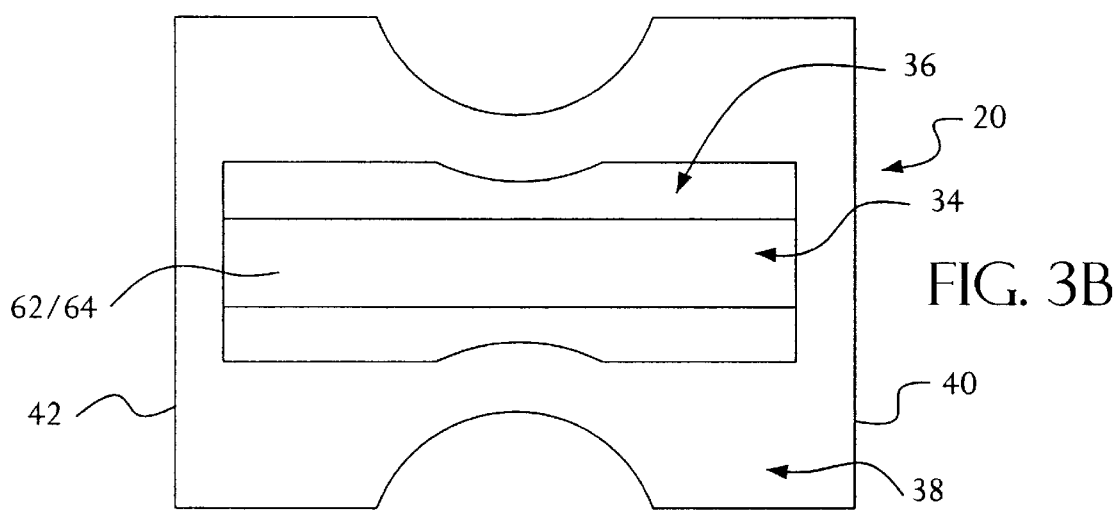
FIG. 3B is a reduced plan like that of FIG. 3A, but utilizing another alternative fluid acquisition system constructed in accordance with this invention.

In FIG. 3B there is shown another embodiment of the fluid acquisition system 34 making use of coextensively sized upper and lower layers, 62 and 64, respectively. However, unlike the embodiment of FIG. 3A, the embodiment of FIG. 3B makes use of an acquisition system 34 whose length is not confined to the target zone, but instead extends the entire length of the core 36. This arrangement, while more expensive than the arrangement of FIG. 3A, provides an additional measure of security by facilitating the transfer the fluid into the core 36 along its entire length. The embodiment of FIG. 3B can be readily fabricated by applying two strips of material forming the two layers 62 and 64 of the acquisition system 34 over the blank of material making up the core 36 and cutting the those layers and the core at the same time. Then the core 36 with the dual layer acquisition system 34 disposed thereon can be placed on the material forming the back-sheet 38 of the diaper to complete the diaper.

Figure 3C:
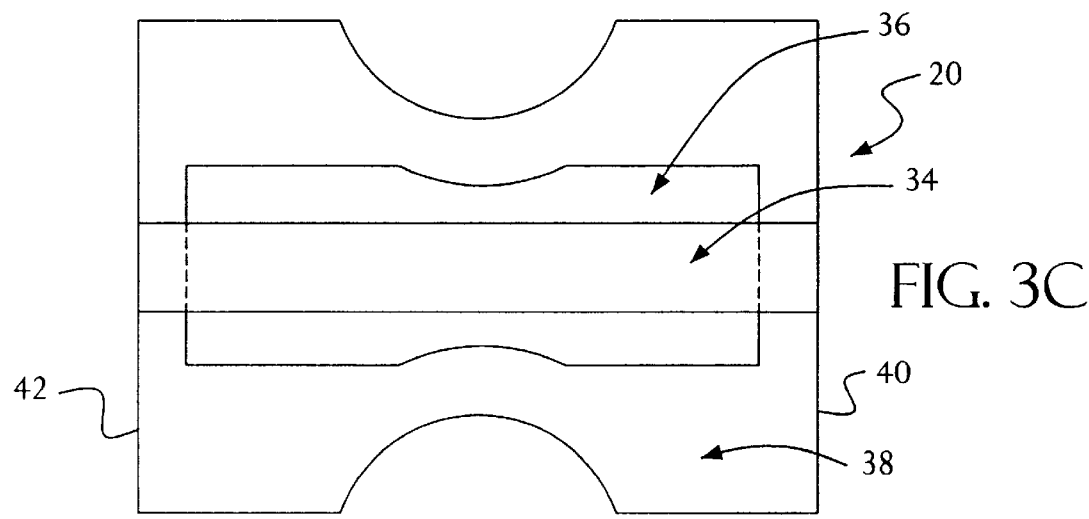
FIG. 3C is a reduced plan view like that of FIG. 3A, but utilizing another alternative fluid acquisition system constructed in accordance with this invention.

In FIG. 3C there is shown still another embodiment of the fluid acquisition system 34 making use of coextensively sized upper and lower layers, 62 and 64, respectively. However, unlike the embodiments of FIGS. 3A and 3B, the embodiment of FIG. 3C makes use of an acquisition system whose length extends the entire length of the diaper 20, i.e., from the front edge 40 to the rear edge 42. The embodiment of FIG. 3C can be readily fabricated by applying two strips of material forming the two layers 62 and 64 of the acquisition system 34 over the blank of material forming the back sheet 38 of the diaper after the core 36 has been cut and placed in position thereon, and then cutting the those acquisition layers at the same time that the diaper's back sheet 38 is cut from the blank of back-sheet material.

Figure 4A:
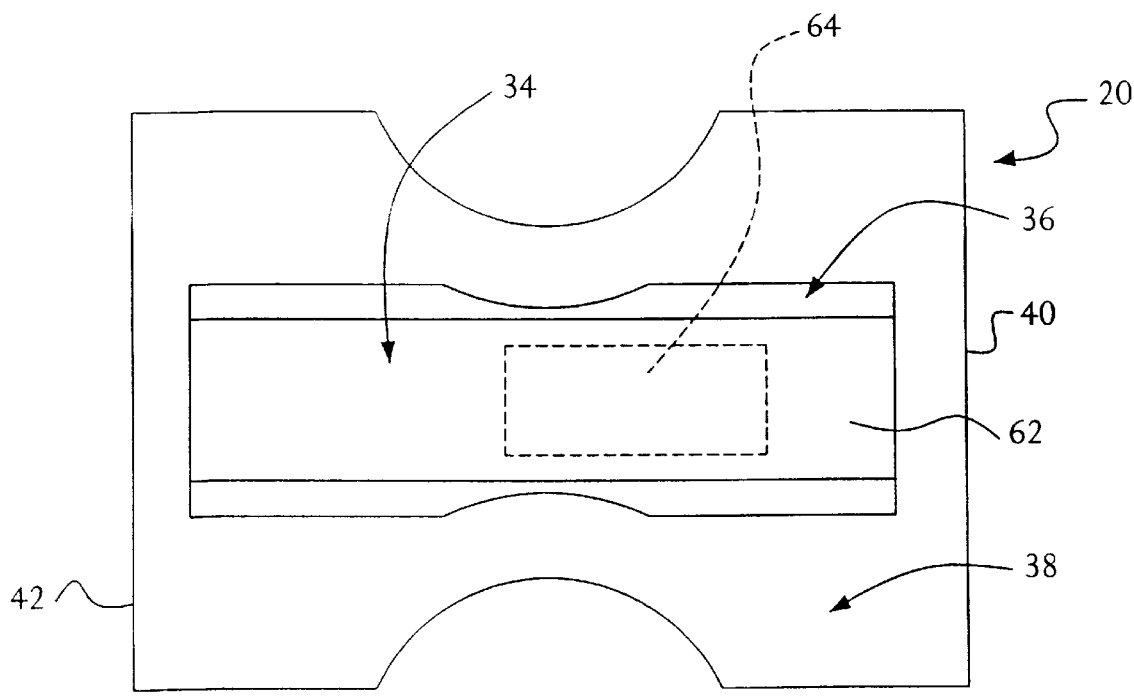
FIG. 4A is a reduced plan view like that of FIG. 3A, but utilizing another alternative fluid acquisition system constructed in accordance with this invention.

In FIG. 4A there is shown one alternative lower cost embodiment of a diaper 20 constructed in accordance with this invention and making use of a less expensive fluid acquisition system 34 than that of FIG. 3B. Thus, in the embodiment shown in FIG. 4A the upper layer 62 is of the same size, shape and location of the upper layer of the fluid acquisition system 34 of FIG. 3B, but the lower layer 64 is significantly smaller, i.e., it is coextensive in size with and located at the target zone. The diaper making use of this type of acquisition system can be readily fabricated by cutting the lower layer 64 and placing it on the blank of material making up the core 36 at the location of the target zone, then placing a strip of material making up the upper layer 62 on top of the lower layer and the blank of material making up the core and cutting the strip and core at the same time. Then the core 36 with the dual layer acquisition system 34 on it can be placed on the material making up the back-sheet 38.

Figure 4B:
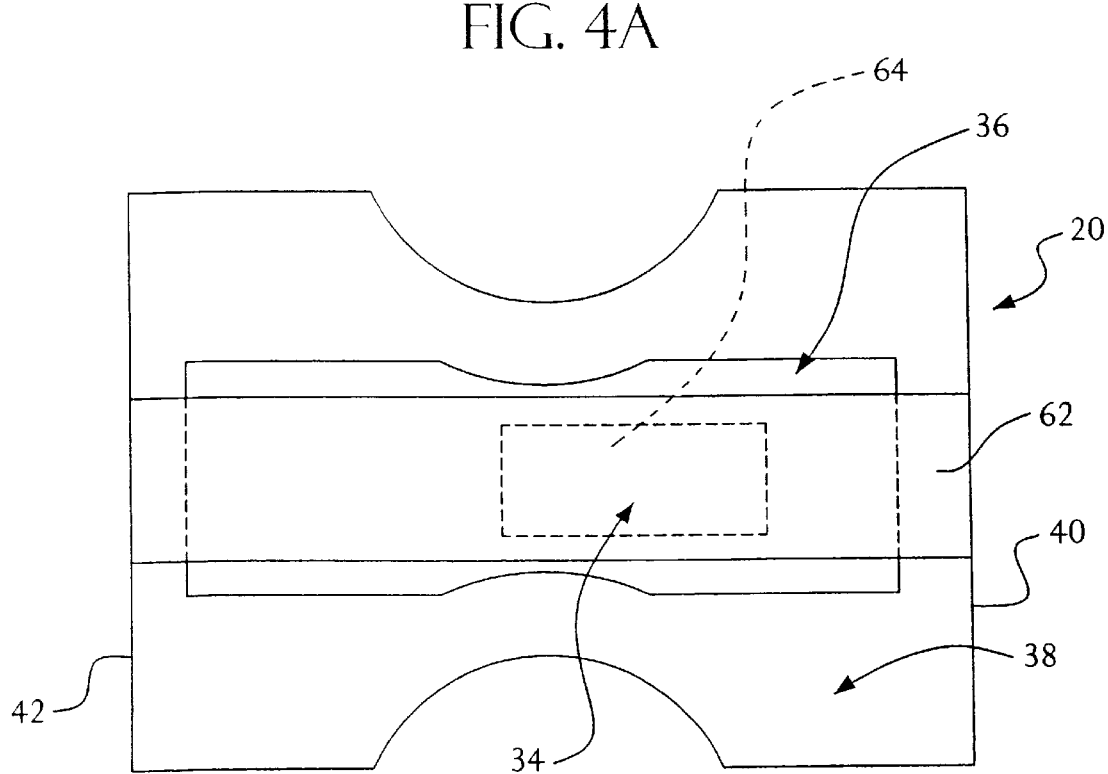
FIG. 4B is a reduced plan view like that of FIG. 4A, but utilizing another alternative fluid acquisition system constructed in accordance with this invention.

In FIG. 4B there is shown another embodiment of the fluid acquisition system 34. This embodiment is similar to the embodiment of FIG. 4A, except that the upper layer 64 (i.e., the apertured film) extends the entire length of the diaper, i.e., from the front edge 40 to the rear edge 42. The embodiment of FIG. 4B can be readily fabricated by cutting the lower layer 64 and placing it on the core at the location of the target zone, then placing a strip of material making up the upper layer 62 on top of the lower layer and the core and cutting the strip at the same time that the back-sheet 38 of the diaper is cut from the blank of material forming the back-sheet.

Figure 5A:
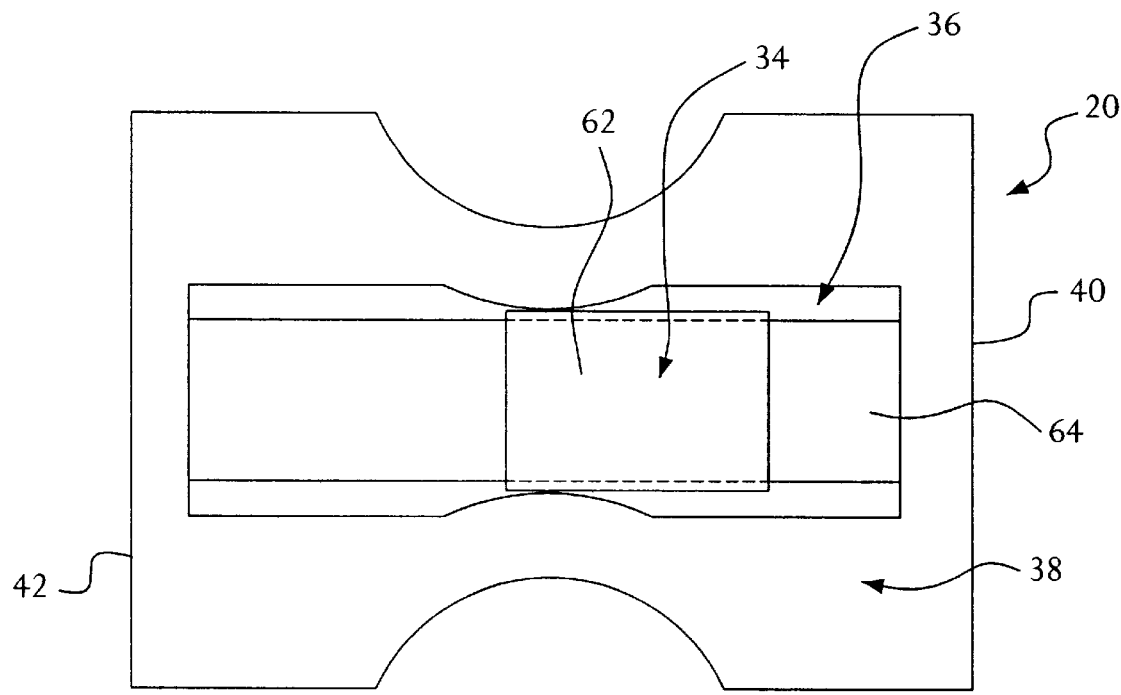
FIG. 5A is a reduced plan view like that of FIG. 3A, but utilizing another alternative fluid acquisition system constructed in accordance with this invention.

In FIG. 5A there is shown another alternative dual layer fluid acquisition system 34 constructed in accordance with this invention. The embodiment of FIG. 5A is similar to that of FIG. 3B, except that the upper layer 62 is smaller than the lower layer and is located over the target zone. Moreover, the upper layer 62 is slightly wider than the lower layer 64. This embodiment is somewhat less expensive than the embodiment of FIG. 3B since it uses less of the lower layer than that embodiment. By using a wider top layer 62, the body-contacting surface of the diaper or other absorbent article in which the acquisition system is used will remain dry over a slightly greater area at the target zone. The diaper making use of this type of acquisition system can be readily fabricated by cutting a strip of material making up the lower layer 64 at the same time that the blank of material making up the core 36 is cut, then a strip of material making up the upper layer 62 is placed on top of the lower layer and the core 36. Then the core 36 with the dual layer acquisition system 34 can be placed on the material making up the back-sheet 38.

Figure 5B:
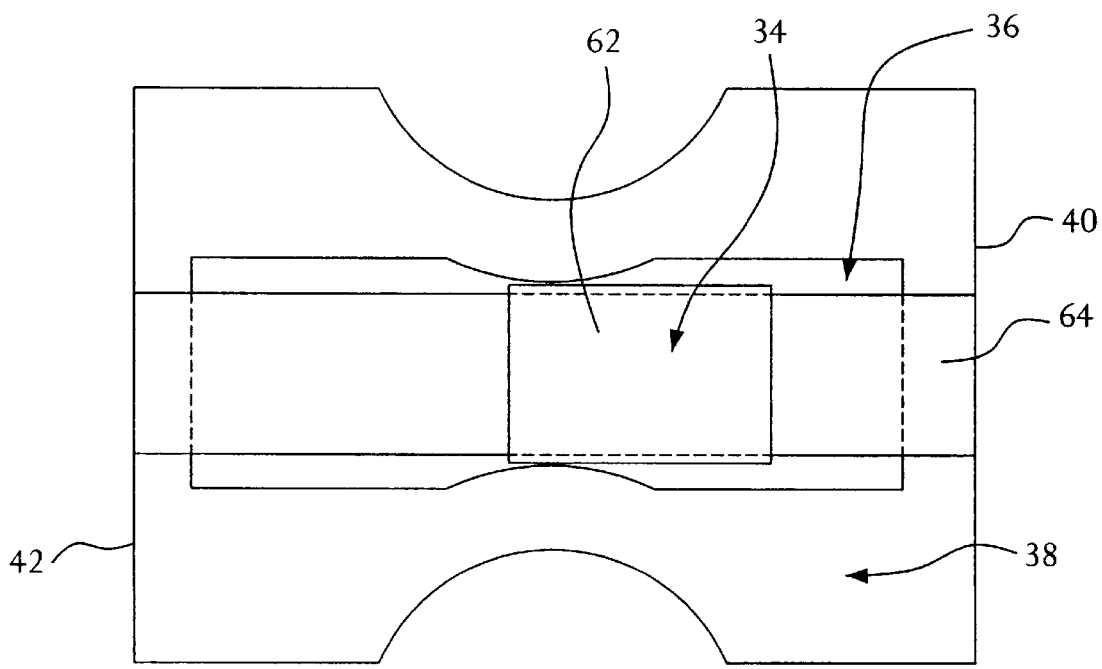
FIG. 5B is a reduced plan view like that of FIG. 5A, but utilizing another alternative fluid acquisition system constructed in accordance with this invention.

In FIG. 5B there is shown another alternative dual layer fluid acquisition system 34 constructed in accordance with this invention. This embodiment is similar to that of FIG. 5A, except that the lower layer 64 extends the length of the diaper and not merely the length of the core. The diaper making use of this type of acquisition system can be readily fabricated by cutting a strip of material making up the lower layer 64 at the same time that the blank of material making up the diaper's back-sheet 38 is cut (after the core 36 has been cut and placed thereon). Then a strip of material making up the upper layer 62 is cut and placed on top of the lower acquisition layer 64.

Figure 6A:
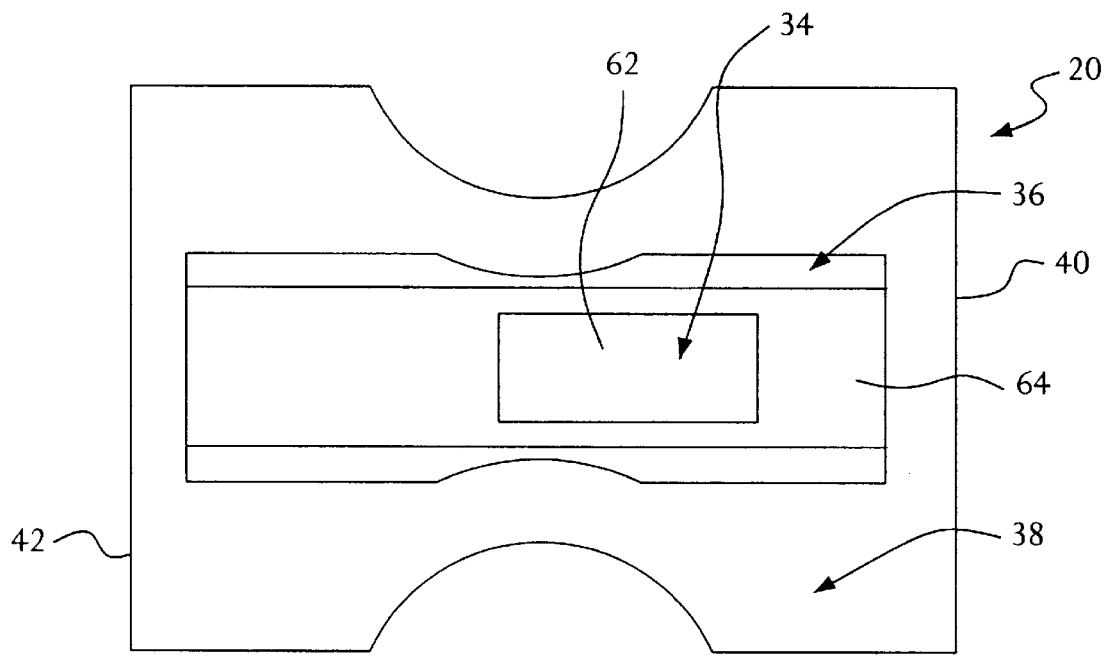
FIG. 6A is a reduced plan view like that of FIG. 3A, but utilizing another alternative fluid acquisition system constructed in accordance with this invention.

In FIG. 6A there is shown another alternative dual layer fluid acquisition system 34 constructed in accordance with this invention. The embodiment of FIG. 6A is similar to that of FIG. 5A, except that the upper layer 62 of FIG. 6A is narrower than the upper layer 62 of FIG. 5A. However, in both embodiments the upper layer is centered over the target zone. This embodiment is somewhat less expensive than the embodiment of FIG. 5A since it uses less of the upper layer than that embodiment. The diaper making use of this type of acquisition system can be readily fabricated by cutting a strip of material making up the lower layer 64 at the same time that the blank of material making up the core 36 is cut, then a strip of material making up the upper layer 62 is placed on top of the lower layer and the core 36. Then the core 36 with the dual layer acquisition system 34 thereon can be placed on the material making up the back-sheet 38.

Figure 6B:
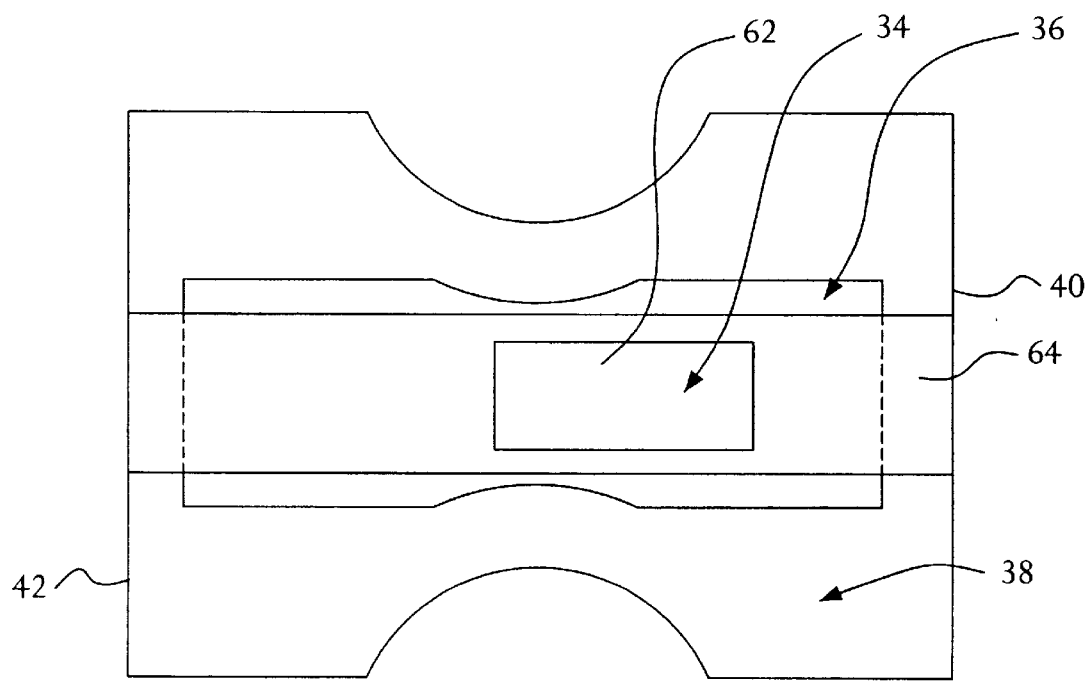
FIG. 6B is a reduced plan view like that of FIG. 6A, but utilizing another alternative fluid acquisition system constructed in accordance with this invention.

In FIG. 6B there is shown another alternative dual layer fluid acquisition system 34 constructed in accordance with this invention. This embodiment is similar to that of FIG. 5B, except that the upper layer 62 of FIG. 6B is narrower than the upper layer 62 of FIG. 5B (and is the same width and length as the upper layer of FIG. 5A). The diaper making use of this type of acquisition system can be readily fabricated by cutting a strip of material making up the lower layer 64 at the same time that the blank of material making up the diaper's back-sheet 38 is cut (after the core 36 has been cut and placed thereon). Then a strip of material making up the upper layer 62 is cut and placed on top of the lower acquisition layer 64.

Figure 7A:
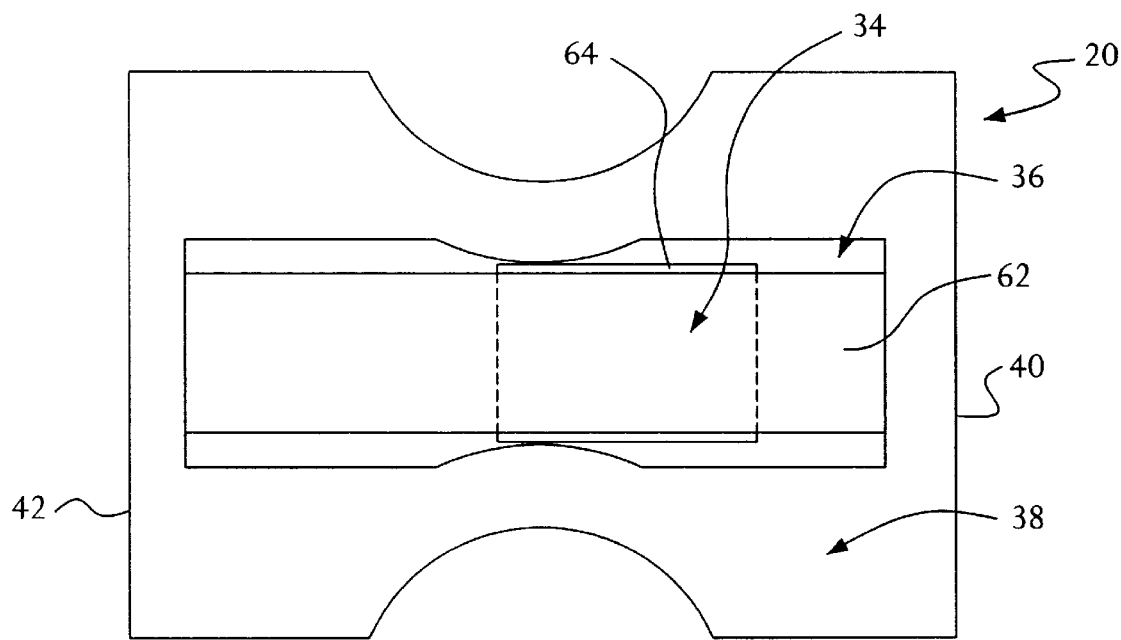
FIG. 7A is a reduced plan view like that of FIG. 3A, but utilizing another alternative fluid acquisition system constructed in accordance with this invention.

In FIG. 7A there is shown another alternative dual layer fluid acquisition system 34 constructed in accordance with this invention. The embodiment of FIG. 7A is similar to that of FIG. 5A, except that the upper layer 62 of FIG. 7A is of the size, shape and location as the lower layer 64 of FIG. 5A and the lower layer 64 of FIG. 7A is of the size, shape and location as the upper layer 62 of FIG. 5A. The diaper making use of this type of acquisition system can be readily fabricated by cutting a strip of material making up the lower layer 64 and placing it on the material making up the core centered at the target zone, then placing a strip of material making up the upper layer 62 on top of the lower layer 64 and the material making up the core and then cutting the core 36. Then the core 36 with the dual layer acquisition system 34 thereon can be placed on the material making up the back-sheet 38.

Figure 7B:
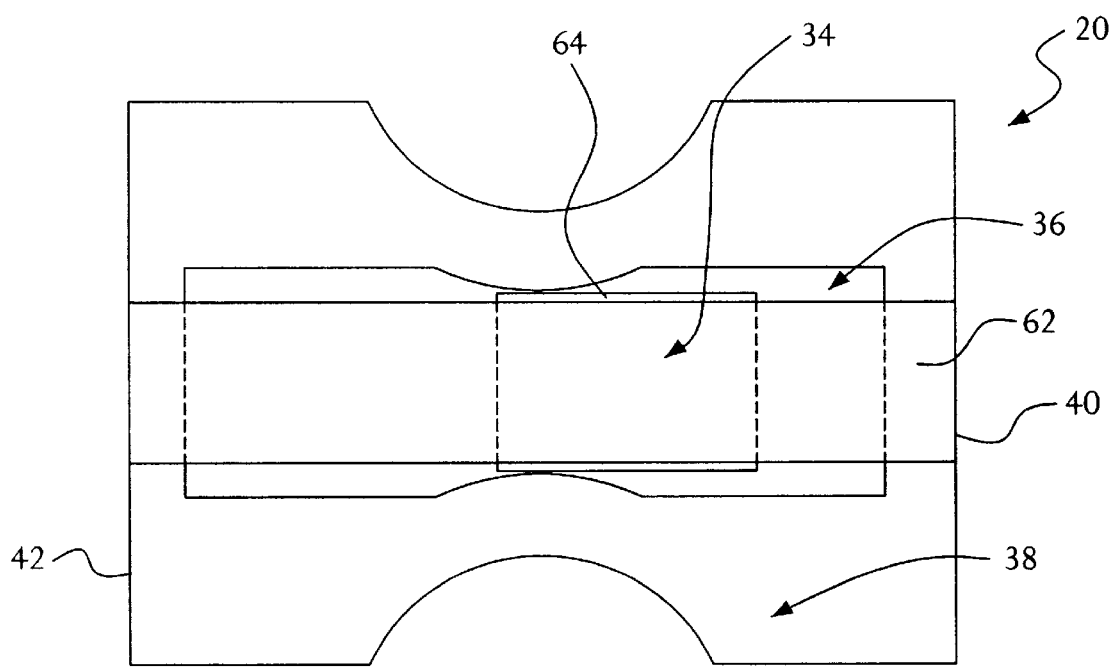
FIG. 7B is a reduced plan view like that of FIG. 7A, but utilizing another alternative fluid acquisition system constructed in accordance with this invention.

In FIG. 7B there is shown another alternative dual layer fluid acquisition system 34 constructed in accordance with this invention. The embodiment of FIG. 7B is similar to that of FIG. 5B, except that the upper layer 62 of FIG. 7B is of the size, shape and location as the lower layer 64 of FIG. 5B and the lower layer 64 of FIG. 7B is of the size, shape and location as the upper layer 62 of FIG. 5B. The diaper making use of this type of acquisition system can be readily fabricated by cutting a strip of material making up the lower layer 64 and placing it on the core 36 centered at the target zone, then the core with the layer 64 on it is placed on the material forming the back-sheet 38. Then a strip of material making up the upper layer 62 is placed on top of the lower layer 64 and the core 36. Then the upper layer 62 and the material making up the back-sheet 38 are cut together.

It should be pointed out at this juncture that the alternative embodiments of the fluid acquisition system described above with reference to FIGS. 3–7 may make use the same materials as used in the embodiment of FIGS. 1–2, described above. Alternatively, a lower basis weight material may be used for the non-woven lower layer 64 than that described with reference to the embodiment of FIGS. 1–2. For example, the lower layer 64 may be formed of an adhesive bonded polyester having a basis weight in the range of 12.8 to 17 gsm. One particularly suitable material is available from BBA of Simpsonville, S.C. Alternatively the lower layer 64 may be formed of spun bond polypropylene with high denier fibers and having a basis weight in the range of 15 to 17 gsm. One particularly suitable material is available from Avgol of Holon, Israel.

As should be appreciated by those skilled in the art from the foregoing the fluid acquisition system 34 of this invention optimizes the fluid penetration rate and volume into the absorbent core 36 below it, while also minimizing the fluid from exiting the diaper 20 when it is saturated and under high stress. The result is a diaper which exhibits high fluid intake and low fluid rewet characteristics, features which are desirable to obtain high absorbency performance with minimal fluid exposure to the wearer's skin.

Without further elaboration the foregoing will so fully illustrate our invention that others may, by applying current or future knowledge, adopt the same for use under various conditions of service.

We claim:

1. A disposable absorbent article arranged to be worn by a wearer to trap and collect fluid waste products of the wearer, said article being suitable accommodating multiple insults of said fluid waste products, said article comprising a longitudinal axis, a top-sheet, a fluid acquisition system, and a fluid absorbent core, said top-sheet having a portion forming a fluid intake zone, said longitudinal axis having a center, said top-sheet portion being formed of a single layer of a fluid pervious fibrous material, said fluid acquisition system comprising a first fluid acquisition layer and a second fluid acquisition layer, said first fluid acquisition layer comprising an apertured film, said second fluid acquisition layer comprising a fibrous, fluid pervious material, said absorbent core comprising a fluid absorbing material suitable for accommodating multiple insults of said fluid waste products, said fluid intake zone making up a portion of the area of said absorbent core and being located along said longitudinal axis offset from said center, said first fluid acquisition layer being located directly over said second fluid acquisition layer and directly under and contiguous with said top-sheet at said fluid intake zone, said second fluid acquisition layer being located under said first fluid acquisition layer at said fluid intake zone and directly over and contiguous with said absorbent core so that said first and second fluid acquisition layers are positioned directly within said fluid intake zone of said top-sheet, and wherein at least one of said first and second fluid acquisition layers is at least coextensive in size with said fluid intake zone and neither of said first and second fluid acquisition layers is coextensive in size with said top-sheet.

2. The disposable absorbent article of claim 1 wherein both of said first and second fluid acquisition layers are at least the size of said fluid intake zone.

3. The disposable absorbent article of claim 2 wherein said first and second fluid acquisition layers are coextensive in size.

4. The disposable absorbent article of claim 1 wherein said first fluid acquisition layer is at least coextensive in size with said fluid intake zone.

5. The disposable absorbent article of claim 4 wherein said second fluid acquisition layer is larger in size than said first fluid acquisition layer.

6. The disposable absorbent article of claim 5 wherein said second fluid acquisition layer comprises an adhesive bonded polyester.

7. The disposable absorbent article of claim 5 wherein said second fluid acquisition layer comprises spun bond polypropylene with high denier fibers.

8. The disposable absorbent article of claim 6 wherein said second fluid acquisition layer has a basis weight in the range of approximately 12.8 to 17 gsm.

9. The disposable absorbent article of claim 7 wherein said second fluid acquisition layer has a basis weight in the range of approximately 15 to 17 gsm.

10. The disposable absorbent article of claim 1 wherein each of said fluid acquisition layers has a predetermined length and a predetermined width, wherein said width of said first and second fluid acquisition layers is the same, and wherein said length of said first and second fluid acquisition layers is the same.

11. The disposable absorbent article of claim 1 wherein each of said fluid acquisition layers has a predetermined length and a predetermined width, wherein said width of is greater than said width of said second acquisition layer, and wherein said length of said first fluid acquisition layer is greater than said length of said second acquisition layer.

12. The disposable absorbent article of claim 1 wherein each of said first fluid acquisition layers has a predetermined length and a predetermined width, wherein said width of said first fluid acquisition layer is greater than said width of said second acquisition layer, and wherein said length of said second fluid acquisition layer is greater than said length of said first acquisition layer.

13. The disposable absorbent article of claim 1 wherein each of said acquisition layers has a predetermined length and a predetermined width wherein said width of said second acquisition layer is greater than said width of said fluid acquisition layer, and wherein said length of said second acquisition layer is greater than said length of said fluid acquisition layers.

14. The disposable absorbent article of claim 1 wherein each of said fluid acquisition layer has a predetermined length and a predetermined width, wherein said width of said second acquisition layer is greater than said width of said first fluid acquisition layer, and wherein said length of said first fluid acquisition layer is greater than said length of said second acquisition layer.

15. The disposable absorbent article of claim 10 wherein said core has a predetermined length and a predetermined width and wherein the width of said core is at least equal to the width of said first fluid acquisition layer.

16. The disposable absorbent article of claim 11 wherein said core has a predetermined length and a predetermined width and wherein the width of said core is at least equal to the width of said first fluid acquisition layer.

17. The disposable absorbent article of claim 12 wherein said core has a predetermined length and a predetermined width and wherein the width of said core is at least equal to the width of said first fluid acquisition layer.

18. The disposable absorbent article of claim 13 wherein said core has a predetermined length and a predetermined width and wherein the width of said core is at least equal to the width of said first acquisition layer.

19. The disposable absorbent article of claim 14 wherein said core has a predetermined length and a predetermined width and wherein the width of said core is at least equal to the width of said first fluid acquisition layer.

\* \* \* \* \*